(12) United States Patent
Jakobovits

(10) Patent No.: US 6,960,447 B2
(45) Date of Patent: Nov. 1, 2005

(54) ISOLATION OF MEMBRANE BOUND LIGAND-SPECIFIC COMPLEXES

(75) Inventor: Aya Jakobovits, Beverly Hills, CA (US)

(73) Assignee: Agensys, Inc., Santa Monica, CA (US)

(*) Notice: Subject to any disclaimer, the term of this patent is extended or adjusted under 35 U.S.C. 154(b) by 0 days.

(21) Appl. No.: 09/932,166

(22) Filed: Aug. 17, 2001

(65) Prior Publication Data

US 2003/0036099 A1 Feb. 20, 2003

Related U.S. Application Data

(60) Provisional application No. 60/308,655, filed on Jul. 27, 2001.

(51) Int. Cl.$^7$ .................... G01N 33/566; G01N 33/567
(52) U.S. Cl. .................... 435/7.21; 435/7.23; 435/7.24; 435/7.8; 435/379; 435/820; 436/501; 436/503; 436/63; 436/86; 436/87; 436/161; 436/173; 436/177
(58) Field of Search .............................. 435/7.21, 7.23, 435/7.24, 7.8, 379, 820; 436/501, 503, 63, 86, 87, 161, 173, 177

(56) References Cited

U.S. PATENT DOCUMENTS 3,843,324 A * 10/1974 Edelman et al.
5,721,120 A * 2/1998 Seifert et al. ................ 435/693

FOREIGN PATENT DOCUMENTS

WO          8403151    * 8/1984
WO      WO 94/25487    * 11/1994

OTHER PUBLICATIONS

Edelman et al, Methods in Enzymology, 34, 195–225, 1974.*
Jakobovits et al, Biochem. Biophys Research Communications, 100, 1484–1490, 1981.*
Kupchik, In John (Ed.), Monoclonal Hybridoma Antibodies, Techniques and Applications, CRC Press, Inc., 1982, pp. 81–89.*
Chevallet et al., Electrophoresis (1998) 19:1901–1909.
Gallagher et al., "The Red Blood Cell Membrane" in Beutler et al., Eds., Williams Hematology, pp. 333–343 (6th ed. 2001).
Guyton & Hall, Eds., Textbook of Medical Physiology, pp. 382–391 (10th ed. 2000).
Link et al., Nature Biotechnol. (1999) 17:676–682.
Molloy et al., Electrophoresis (1998) 19:837.
Neubauer et al., Proc. Natl. Acad. Sci. USA (1997) 94:385–390.
Rudert et al., Biotechnol. Ann. Rev. (2000) 5:45–86.
Rutishauser et al., Proc. Natl. Acad. Sci. (1973) 70(12)3894–3898.
Parker et al., Journal of Biological Chemistry (1984) 259(15):9906–9912.
Supplementary European Search Report for EP 02756793.2 mailed on Aug. 3, 2004, 2 pages.

* cited by examiner

*Primary Examiner*—David Saunders
(74) *Attorney, Agent, or Firm*—Morrison & Foerster LLP

(57) ABSTRACT

A method to recover receptors without removing microenvironmental components associated with them is described. The membranes containing the receptors are first associated with ligand-coupled solid supports to achieve association of the membranes through a receptor/ligand complex which includes the microenvironment to the solid support and then removing the membrane from the receptor and its microenvironment by shear forces. The thus isolated receptors and their microenvironments can then be analyzed for their role in cellular differentiation, apoptosis, transformation and the like.

24 Claims, 1 Drawing Sheet

Isolation of Membrane Antigens and Their Associated Complexes by Plucking

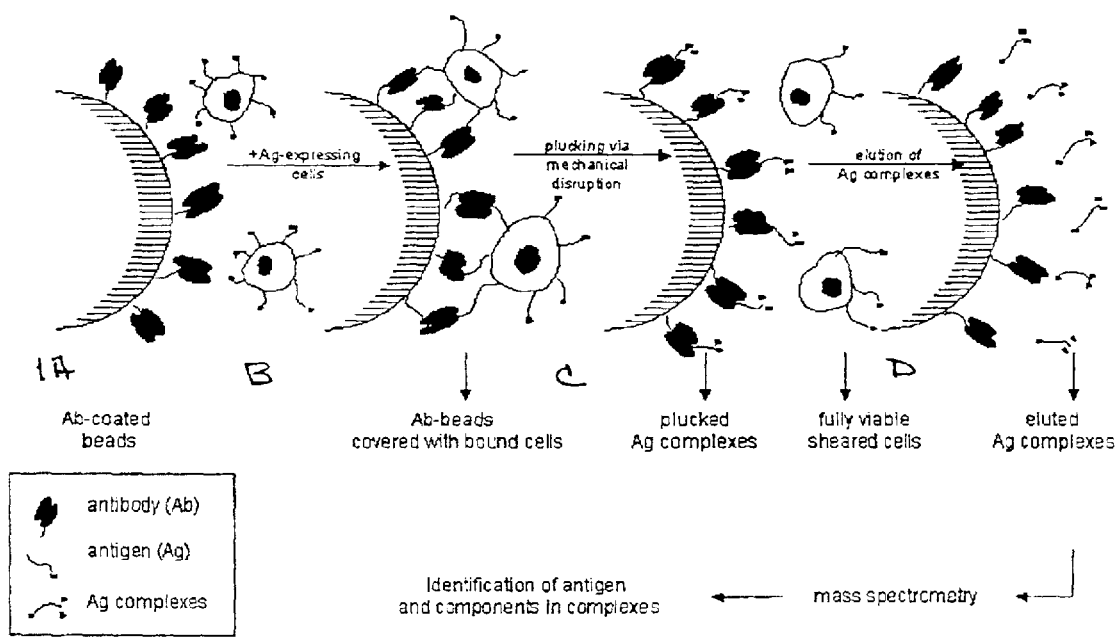
Isolation of Membrane Antigens and Their Associated Complexes by Plucking

ISOLATION OF MEMBRANE BOUND LIGAND-SPECIFIC COMPLEXES

CROSS-REFERENCE TO RELATED APPLICATIONS

This application claims priority under 35 U.S.C. § 119(e) to Ser. No. 60/308,655 filed 27 Jul. 2001. The contents of this application are incorporated herein by reference.

FIELD OF THE INVENTION

The invention relates to methods to isolate membrane-bound complexes wherein the microenvironment of a membrane-bound protein that is bound by a specific ligand is preserved. More specifically, the invention concerns non-destructive preparation of membrane-bound, especially cell surface receptors, along with the molecules with which they are associated.

BACKGROUND ART

A multiplicity of procedures for isolation of proteins is available and practiced in the art. For soluble proteins such as those that occur in the cytoplasm, direct application of these techniques is possible, as it is unnecessary to take steps to free these proteins from their surroundings. However, proteins or lipids that are membrane-bound, have required harsher treatment to release them from the membrane. One commonly employed technique is solubilization using detergents, or other harsh reagents such as chaotropic agents or other denaturing compounds such as urea. See, for example, Molloy, M. P., et al., *Electrophoresis* (1998) 19:837–834; Chevallet, M., et al., *Electrophoresis* (1998) 19:1901–1909. A drawback of such methods is that the isolation process goes too far, i.e., the protein is recovered essentially by itself, and is unaccompanied by the cellular membrane components that normally are associated with it and which are often crucial to its biological function. Elucidation of the biological role of such proteins requires knowledge of the substances involved in transduction of signals resulting from binding of the protein to its specific ligand. Thus, it would be extremely valuable to recover these membrane proteins along with their corollary substances, so that the nature of these substances and the biological role of the protein and its associated substances can be determined. It will be noted that the corollary substances may be associated themselves with the membrane or may be associated with the receptor in the cytoplasm.

Another drawback of the prior art methods is that in some instances, the membranes are sufficiently disrupted by the harsh reagents that cryptic receptors become exposed and coincidentally bind to ligands of interest. Thus, the practitioner is misled into analyzing a receptor with respect to a ligand when in fact the receptor is irrelevant to the biological function of the ligand in question.

A description of one method to obtain lectin receptors from erythrocytes without the use of detergents was described by Jakobovits, A., et al., *Biochem. Biophys. Res. Commun.* (1981) 100:1484–1490. In this method, erythrocytes were treated with neuraminadase and then with lectin-coated, i.e., peanut agglutinin-coated sepharose beads, thus resulting in coupling the erythrocytes to the beads through an interaction between lectin and the cognate receptors on the cell surface. Unbound cells were removed and the pellet of erythrocyte-covered beads was pipetted vigorously with a Pasteur pipette. The beads were then washed to remove any erythrocytes that had been sheared, and it was determined that most erythrocytes could be removed by repetition of this treatment. Any remaining bound cells could be removed by quick vortexing and subsequent wash. While the erythrocytes were removed, the receptors coupled to lectin remained bound to the sepharose beads. These "plucked" receptors were then released from the beads by boiling or by competitive elution with galactose.

The elution of the bound components resulted in recovery of the lectin binding components designated asialoglycophorins. This work showed that cells lacking nuclei, when treated to expose the relevant sugars, could be bound through carbohydrates on their surfaces to agglutinins (i.e. lectins) and that the carbohydrate-containing moieties bound to the agglutinins could be removed from the cell membranes by mechanical disruption. No description of any non-covalently associated components removed along with the glycoprotein receptors per se was provided. Further, there is no description of cells which had not been treated to expose the relevant sugars, nor was there a suggestion to employ ligands other than lectins. As noted below, lectins are relatively non-specific and thus will bind to a multiplicity of glycosylated proteins some of whose biological functions are irrelevant to the specific nature of the lectin. While effective binding of cells can more readily be achieved through the use of lectins than through the specific ligands of the present invention, the resultant does not provide information regarding biologically relevant receptors due to the non-specificity of lectin binding. Some lectins do engender biological responses, and lectins are specific with respect to the carbohydrates to which they bind, but the individual carbohydrate targets are promiscuous with respect to the receptors in which they reside, thus, as regards individual receptors, specificity of binding is lost.

DISCLOSURE OF THE INVENTION

It has now been found that surface receptors comprising protein, in particular in nucleated cells, can be removed along with non-covalently associated complexed components by specific binding of these receptors to counterpart ligands and subsequent shearing of the bulk of the cell or of the relevant membrane from the ligand/receptor complex. If desired, the receptor, along with its associated cellular components, can be dissociated from the specific ligand using, for example, competitive binding by the receptor itself or its analogs or a number of other techniques.

The invention provides a method to rapidly and specifically isolate membrane-bound components such as cell surface receptors in their native conformation and in their native microenvironments, under conditions wherein the status of the component or receptor is preserved, thus permitting insights into the function of the receptor that are unavailable when conventional methods for isolation are used. Such conventional methods typically involve detergents or chaotropic agents which distort and/or disrupt the membrane and cytoplasmic environment surrounding the receptor and thus obliterate information as to the environment and function of the receptor itself. The invention method thus provides information which identifies and characterizes cell surface targets that interact with stimuli/ligands and for the identification and design of molecules that interact with these targets. The identification and design of molecules that interact with these targets, including molecules that inhibit them, is further informed by the understanding made available by the methods of the invention which elucidate the manner of function and additional cellular components associated with the targets.

Thus, in one aspect, the invention is directed to a method to isolate a membrane-bound receptor such as a cell surface receptor along with its microenvironment which method comprises providing a solid support coupled to a ligand specific for the desired receptor, to which membranes bearing the receptor have been bound through association with the ligand to form a ligand/receptor complex, and then shearing the cells from the ligand/receptor complex. The receptor thus recovered will remain associated with its microenvironment. The microenvironment, of course, may in fact not include any associated cellular components and the receptor will be recovered alone. This, too, is valuable information concerning the nature of the receptor. This may optionally be followed by dissociating the ligand/receptor complex (comprising the receptor and its microenvironment) from the solid support and/or dissociating the ligand from the receptor/microenvironment to recover the receptor/microenvironment itself. In any event, as the microenvironment remains associated with the receptor, it is an additional step that can be included within the invention to analyze the microenvironment to determine what, if any, components it contains. Numerous methods are available for such analysis, including, for example, chromatographic analysis, mass spectroscopy, 2-dimensional gels and Western blots.

In a preferred method of the invention, the ligand is specific for the receptor per se, and does not cross-react with receptors irrelevant to biological activity of the target receptor. As defined hereinbelow, ligands specific for receptors do not include lectins. Lectins lack the requisite ability to bind only to unique biologically significant receptors. The lectins generally are able to bind to carbohydrates associated with proteins, and thus are cross-reactive with glycosylated proteins in general. They bind to higher densities of receptors on cells as compared to more specific ligands, such as antibodies. It should be noted that antibodies used as ligands need not themselves result in any biological response; however, they specifically target receptors whose ligands do elicit a response.

Further, lectins, in order to bind may require pretreatment of the surface of the membrane to expose the carbohydrate moieties which they bind. A preferred method of the invention utilizes membranes which have not been subjected to any surface treatment that modifies the carbohydrates exposed on the cell surface. In a preferred embodiment, an advantage is that the membrane is employed in a more realistic native state. In this preferred method, there is no surface treatment of the membranes prior to contacting them with the specific ligand.

In still another preferred embodiment, the membranes are associated with or derived from a nucleated cell or a bacterial cell, preferably a nucleated cell. Nucleated cells are representative of virtually all typical eukaryotic cells with the exception of red blood cells. The membranes on the surface of, or contained in nucleated cells are inherently more complex than those associated with, for example, red blood cells. Further, nucleated cells perform more complex metabolic functions than red blood cells and thus offer a more fertile substrate for retrieval of receptors.

In still another preferred embodiment, the method of the invention includes the active steps described above to analyze the microenvironment in which the receptor is contained. The microenvironment may reside in the membrane itself or in the proximity of the receptor in the cytoplasm. As stated above, the microenvironment may not contain any closely associated components, and thus the method of the invention will result in isolation of the receptor per se.

In another aspect, the invention is directed to a method to obtain a library of membrane-bound receptors, which method comprises providing solid supports coupled to a multiplicity of ligands; contacting the solid supports with a sample of membranes, preferably from or associated with nucleated cells, under conditions whereby receptors in said membranes or on said cells are coupled to one or more of the ligands on said solid supports, so that a ligand forms a complex with its cognate receptor. The membranes or cells are then dissociated from the ligand/receptor complexes which comprise the receptor and microenvironment. The membrane-derived receptors (with microenvironments) are optionally recovered, either alone or along with their ligands, from the solid support. The receptor/microenvironment can then be analyzed to determine what, if any, components are associated with the isolated receptor.

In additional aspects, the invention is directed to isolated receptors associated with microenvironments prepared by the method of the invention and to novel receptors identified thereby. The recovered receptors can be used in screening assays to identify compounds which agonize or antagonize them. The recovered receptors can further, if the receptors are identified as associated with undesired or diseased cells, be used in the design of antibodies, pharmaceuticals or vaccines to target these cells.

The invention also includes receptor profiles of membrane or cell samples. As further described below, the method of the invention can be used in a high throughput system to determine patterns of receptors at the cell surface or contained in the membrane.

Thus, an important aspect of the invention is the ability to characterize interactions with receptors and the cellular networks associated with their functions.

BRIEF DESCRIPTION OF THE DRAWINGS

FIG. 1 is a schematic diagram illustrating the method of the invention.

MODES OF CARRYING OUT THE INVENTION

The invention provides, for the first time, a method whereby at least three important goals are achieved. First, the method permits the isolation of membrane-bound receptors that bind specifically to a ligand in a form which preserves their native conformations and associated moieties, thus providing a wealth of information about the receptors and the components with which the receptors are associated and thus the functions and roles of the recovered receptors that has previously been unavailable. By ascertaining the nature of moieties that are natively associated with the receptors, the role of the receptor in cellular pathways, such as proliferation, differentiation, survival, apoptosis, transformation and the like can be determined. Once such roles are determined, the receptor itself can be employed in the design of appropriate strategies to control the relevant function. Second, and related to the first goal, is the assurance that the receptors retrieved are not artifacts of the experiment by avoiding the use of agents that would reveal cryptic molecules which are not of biological significance, but which coincidentally bind the ligand used. Third, the method of the invention offers a high throughput system for rapid identification of membrane-bound receptors through a facile system of recovering these receptors from membranes. Some receptors identified may be previously unknown.

The identification and characterization of protein-protein, protein-lipid, or any other type of interaction exhibited by the receptors is significant in evaluating the biological role of the receptor, and thus the biological role of ligands to which it may be bound.

As used herein, "receptor" refers to any moiety which specifically binds to a cognate ligand. Typically, the receptors are proteins and may or may not be further derivatized such as through glycosylation, lipidation, coupling to additional structural components and the like. "Receptors" is used herein as a generic term and is not limited to proteins that are necessarily associated with a cellular pathway. Membrane-associated receptors include, for example, G-protein coupled receptors, cytokine receptors, ion channels, opioid receptors, hormone receptors, retinoid receptors, steroid receptors, growth factor receptors, integrins, immunoglobulins, T-cell receptors, MHC class I and II and, generally, any membrane-bound protein which comprises sufficient exposure at the surface of the membrane to bind specifically to a ligand.

The "ligand" may be any cognate binding agent other than a lectin which is specific for a membrane-bound receptor component where the component is characteristic of one or several receptors. (A characteristic component may be shared by several receptors, not all of which need have the same biological function, though this is thought to be the exception.) That is, the ligand should interact only with receptors that it agonizes or, in the case of antibodies or other mimics of the native ligand, only the receptor activated by the native ligand. Lectins are excluded from the definition of ligands because they are relatively non-specific. "Lectin" is a generic term which includes proteins that bind to carbohydrate residues. As many proteins are glycosylated, lectins bind large numbers of proteins non-specifically. In addition, the use of lectins may require treatment of the membranes prior to contact in order to expose carbohydrate residues that are masked, for example, by sialic acid residues. Thus, "ligand" as herein defined includes a range of substances which bind highly specifically to a particular receptor as opposed to lectins which may bind a multiplicity of receptors.

The ligand may be a ligand which is native to the receptor—for example, a cytokine which normally binds a cytokine receptor, but may also be a synthetic compound which is designed for specific binding, including antibodies or fragments thereof. In terms of their chemical nature, the ligand may be a protein, a lipid, a sugar or a small molecule. The ligand may have other characterizing features such as comprising an immunoglobulin structure or fragment thereof, activity as a toxin, enzyme, or other biological activity.

Thus, with the exception of lectins, as noted above, as used herein, "receptor" and "ligand" refer simply to a cognate binding pair wherein the receptor is associated with a membrane and the ligand, typically, is not.

"Protein," "peptide," and "polypeptide" are used interchangeably, regardless of the length of amino acid sequence included.

As used herein, the term "microenvironment" of the receptor refers to the molecules in the immediate surroundings of the receptor and with which it is noncovalently associated. These molecules may be involved in the transduction of signals from interaction of the receptor with its ligand, or may be molecules that are activated or deactivated by interaction with the receptor. These molecules may interact constitutively with the receptor or may be interactive only upon its binding to a ligand. These molecules may reside in the membrane itself, or may be associated with the receptor in the cytoplasm. It is the nature of these molecules in the immediate microenvironment of the receptor which provide important information as to the role, mechanism of action, and/or kinetics of the receptor in cellular functioning. This assessment may be critical in a decision as to whether the action of the receptor should be agonized or antagonized, and as to whether it is useful to construct antibodies, proteins, cells, pharmaceuticals or vaccines which specifically interact with the receptor or elicit an immune response thereto. In addition, an understanding of molecules associated with the receptor will aid in the design of screening assays for identification of useful therapeutic and prophylactic agents.

The membranes used as the starting material in the invention may retain their association with their cells of origin or may be separated therefrom. For use as starting materials in the method of the invention, it will have been unnecessary to subject the membranes to any "surface treatment," as would, for example, expose shielded carbohydrates or cryptic receptors. "Surface treatment" means treatment designed to expose portions of the receptors not natively displayed by the membrane. Such surface treatments may include, for example, treatment with neuraminadase to expose carbohydrate residues; such treatment would be unnecessary within the context of the present invention as lectins are excluded from the ligands specifically binding receptors as described above. Indeed, one of the drawbacks of prior art methods to recover membrane-displayed receptors is that treatment with detergents or other harsh reagents may expose cryptic moieties which bind the ligand used in the method, thus creating an artifact uncharacteristic of the native function of the ligand. Thus, "surface treatment" is avoided so as to ensure that the membrane displays only portions of the receptors that are displayed in the native state of the membrane.

However, the "microenvironment" may in fact be devoid of any interacting substances. In this case, the receptor will be isolated absent any associated materials; i.e., the microenvironment is a void. Thus, "microenvironment" should not be understood to mandate the presence of additional substances when the receptor is recovered by the method of the invention. Where the "receptor" is unassociated in any meaningful way with additional substances, it will be isolated by itself and this, too, provides valuable information.

Typically, the membrane with which the receptor is associated is a cell surface membrane. However, the invention is also applicable to recovery of receptors which are associated with other cellular membranes, such as nuclear membranes, endoplasmic reticulum, golgi apparatus, mitochondria or other cellular organelles. In applying the method to intracellular receptors, nuclei or other organelles are first isolated and subjected to the method of the invention in place of intact cells. Cell surface membranes may also be isolated from the cells; however, in the case of cell surface membranes, intact cells may also be used.

Any type of cell or tissue which contains exposed receptors can be used in the method of the invention. Such cells include, generally, eukaryotic cells, such as yeast cells, fungal cells in general, cells derived from invertebrates, and bacterial cells. However, the cells employed in the invention are preferably nucleated cells and can include any cell which displays receptors at its surface. Preferably, such cells are vertebrate cells, and most preferably mammalian cells.

A wide variety of such cells is employed, including, without limitation, cells from adipose, areolar, connective, elastic, epithelial, neural, mucous, reticular, etc. tissues. Cells can be from alimentary, breast, cardiovascular, cutaneous, endocrine, gastrointestinal, hematopoetic, hepatobiliary, lymphoid, lymphoreticular, muscle, male or female reproductive, respiratory, skeletal, or urinary tract tissues. Thus, cells can comprise hematopoietic cells, including lymphocytes of various types, progenitor cells, stem cells, macrophage, granulocytes. Cells can comprise endothelial cells, myeloid cells, tumor cells, cells derived from a various of cell lines, and cells derived from a variety of organs such as urinary bladder, brain, breast, colon, heart, kidney, liver, lung, bone marrow, ovary, pancreas, prostate, skin, stomach, testes, and the like. Highly tissue-specific cells, such as those derived from the retina, cornea or choroid can also be used. Specialized cells of the immune system, or cells associated with tumors which contain tumor-associated antigens at their surfaces can also be employed.

Thus, receptors associated with membranes contained in or on tumor cells, such as those derived from benign or malignant tumor cells of prostate, bladder, kidney, colon, breast, pancreas, bone, ovary, lung, brain or non-solid tumors such as lymphomas and leukemias are available for retrieval and study according to the method of the invention. In addition, membranes derived from cells associated with various disease conditions, including infected cells, cells exhibiting an autoimmune response, or cells with other abnormalities are made available for elucidation of pathways and receptors unique to these cells.

An advantage of the invention is that a wide variety of cell types can be assessed for the types of receptors displayed and thus the role of these receptors in cell differentiation and growth further elucidated. The methods of the invention also permit profiling of the receptor pattern on particular types of cells and affords the ability to contrast the membrane receptor profile in cells which are associated with particular tissues, or at particular stages of differentiation, aging, or which are considered abnormal, such as diseased cells or tumor cells.

In one application of the invention, a single receptor along with its microenvironment is removed from the cell surface or other cellular membrane of choice. In this embodiment, there is first provided a solid support to which is bound a ligand for the desired receptor. If the receptor is known, a convenient ligand is an antibody or fragment thereof that is immunospecific for the receptor. Such antibodies can be prepared by immunization with the previously isolated receptor (such previous isolation generally having destroyed the microenvironment of the receptor) or with cells displaying the receptor using standard immunization techniques or using phage display technology. Polyclonal antibodies which are immunospecific for the receptor can then be recovered from the sera of an immunized subject, or monoclonal antibodies may be prepared from the subject. Antibodies can also be prepared recombinantly in various forms such as single-chain antibodies. Fragments of the antibodies, such as Fab, Fab' and F(ab')$_2$ may also be used. Any portion of the antibody which is immunospecific can be used as the ligand for recovery of the receptor.

Even if the receptor is not known, antibodies can be prepared which result in the isolation of the previously unknown receptor along with its microenvironment containing whatever components the microenvironment may include. For example, cells may be used for immunization and monoclonal antibodies prepared from the subject of immunization and produced by hybridoma technology or using standard recombinant techniques including phage display. The individual monoclonal antibodies can then be used as ligands to retrieve previously unknown receptors from the cell surfaces or from membranes derived from these cells.

In addition to antibodies, aptamers which specifically bind the receptor can be obtained using Selex™ procedures as is understood in the art. Alternatively, the ligand may be a ligand native to the receptor or may be an arbitrarily chosen ligand recovered, for example, from a combinatorial library, including libraries which contain small molecules, peptides, antibodies and the like.

The now selected ligand is coupled to a solid support so that a receptor to which the ligand is complexed is recoverable. The solid support may be in any convenient form, including, for example, beads composed of polystyrene, latex, Sephadex, polyacrylamide and the like. Also employable are magnetic beads, fibers and other geometric configurations. Particularly convenient are multi-well plates.

The ligand is coupled to the solid support by any convenient means wherein the binding is sufficiently tight to withstand disruption by shearing. Preferably, but not necessarily, the ligand is covalently bound to the support. Depending on the choice of ligand and the chemical nature of the support, linking techniques are selected to obtain the desired binding. Such linking techniques include, for example, coupling through CNBr, or coupling through linkers, such as those available from Pierce Chemical Co., Rockford, Ill. Coupling can be through peptide linkages, disulfide linkages, cross-linking through glutaraldehyde, biotin/avidin binding and the like. The linkers can also include means for dissociating the ligand from the solid support. For example, the linker may include a photocleavable portion or a portion which is cleavable by specific enzymes or in response to a predetermined reagent which is harmless to the ligand or the receptor to be retrieved. The selection of linking techniques will be apparent to the skilled artisan.

The solid support, having been provided with, preferably, covalently bound ligand, is then treated with the cells, tissues or membranes containing the desired receptor. The membrane may be included in an intact cell or tissue, an intact nucleus or organelle, or may be prepared as an isolated membrane per se. The ligand-derivatized solid support is then treated with the membrane that contains receptor under conditions wherein a complex is formed between the receptor and the coupled ligand. These conditions are typically physiological conditions of neutral pH, room temperature or slightly higher or lower, and, if intact cells are used, preferably appropriate osmotic pressure. The contact time varies but may be as short as one minute or as long as several hours or overnight. After sufficient time has elapsed that a complex between ligand and receptor is formed, the solid support is removed from the sample that contains the membranes and optionally washed to remove unbound membrane, cells or organelles. Washing is generally under standard physiological temperature and pH as well. The now-recovered solid support thus contains ligand complexed to receptor wherein the receptor remains embedded in the membrane of the intact cell, nucleus, or membrane preparation.

The next step is to dissociate the receptor/ligand complex from the membrane in which the receptor resides. In order to perform this step, a gentle force, such as a shear force, is applied. This force can be obtained in a variety of ways, including vortexing, extrusion, such as through vigorous repetitive pipetting, shaking, sonication under mild conditions, stirring, or any other method to impose a gentle shear force. The shear is such that the receptor/ligand complex remains intact while the receptor, along with associated moieties is removed gently from the membrane in which it has resided. The receptor, thus, continues to be associated with the molecules it interacts with in situ. If intact cells or tissues have been used, the cells or tissues remain intact and viable. The fact that they are not lysed permits avoidance of contamination with debris released from lysed cells or tissues. This step may be referred to as "plucking."

After the receptor along with its microenvironment has thus been removed from the membrane, the receptor and its associated components can be analyzed and identified either on the solid support or after removal therefrom. Removal of the receptor from the solid support can be effected, for example, by competitively dissociating the ligand/receptor complex, by cleavage of the entire ligand/receptor complex from the support by releasing the ligand from the support, or by providing dissociation conditions whereby the ligand/receptor complex is disrupted. For example, if the ligand is an antibody, an antigen which binds the antibody in competition with the receptor can be used to compete the receptor away from binding to the solid support. Such dissociation can also be achieved by altering the conditions so that the ligand no longer binds to a receptor, for example, by altering the pH. If the linkage used to couple the ligand to the solid support has been designed to include a photocleavable portion, the entire complex can be removed by exposure to the appropriate wavelength of light. If the linkage of ligand has been designed to include an enzyme cleavage site, the solid support is then treated with the appropriate enzyme. Alternative ways to dissociate the ligand/receptor complex to free the receptor and its microenvironment alone would include, as well as competitive binding, treatment with high temperatures or with solvents or pH conditions which result in the dissociation. However, competitive interaction is preferred as alternative methods for dissociation of the complex may also dissociate the receptor from the components of its microenvironment.

The further analysis and identification of the receptor and its associated components is then conducted by means generally known in the art. The protein may be sequenced, and the protein, its post transcriptional modifiers and the accompanying materials of the microenvironment may be analyzed by chromatographic methods, NMR, mass spectrometry, infrared spectrometry and the like. A various of analytical tools is now available for characterizing the protein itself and its microenvironment. Two dimensional electrophoresis, Western blot, and mass spectrometry, and by analytical means which discern protein-protein interactions may be used. See, for example, Rudert, F., et al., *Biotechnol. Ann. Rev.* (2000) 5:45–86; Link, A. J., et al., *Nature Biotechnol.* (1999) 17:676–682; Neubauer, G., et al., *Proc. Natl. Acad. Sci. USA* (1997) 94:385–390. The contents of these documents is incorporated herein by reference to demonstrate the nature of these techniques.

One illustrative embodiment of the invention is shown in FIG. 1. As shown (FIG. 1A), beads are coated with an antibody specific for an antigen expressed at a cellular surface. The antibody-coated beads are exposed to the antigen-expressing cells resulting in formation of complexes between the antibody and the antigens at the cell surface (FIG. 1B). The cells that are bound to beads are then "plucked" using, for example, shearing (FIG. 1C), leaving behind the antibody complexed to the antigen and its associated membrane components. The cells which are sheared from the complex are typically fully viable. In the illustrative procedure in FIG. 1, the antigen with its associated membrane components is then eluted from the antibody/antigen complex (FIG. 1D) and subjected to analysis, for example, by mass spectrometry to identify the antigen and the components in the complexes, as described above.

The method of the invention can be used for the recovery and analysis of both receptors whose presence was already generally known and to recover receptors which were previously unidentified. To recover unidentified receptors, the specific ligand may be arbitrarily chosen, and can comprise a plurality of arbitrarily chosen receptors. For example, it may be desirable to recover any membrane-embedded receptor which can complex with a particular steroid or with a particular cytokine or with a particular opioid or with a particular antigen or antibody.

Alternatively, it may be desirable to recover a multiplicity of receptors non-specifically. This can be accomplished using the method of the invention by providing the portion of the receptor exposed on the membrane with one member of a specific binding pair, such as generically biotinylating the proteins at the membrane surface and then utilizing avidin as the ligand. The recovered receptors are then separated by electrophoresis, and analyzed as described herein.

The method of the invention can also be adapted to high throughput screening to permit identification of receptors to a multiplicity of ligands. For example, separate portions of a solid support may be coupled to a multiplicity of ligands and the multiplicity of ligands then interacted with a sample of membranes which, as before, may comprise intact cells, intact nuclei, intact organelles, or membrane preparations per se. The receptor profile of the membrane preparation can then be ascertained in detail.

Initially, the array of ligands bound by the membrane preparation can be ascertained by labeling the membranes (or cells or nuclei) and detecting the presence of label on a solid support. This can be done, for example, by utilizing fluorescent, colorimetric, radiolabels, or other well known techniques to render the membranes detectable, or by secondarily labeling the membranes by reaction with labeled reagent, such as labeled antibody. The method of the invention of recovering the receptor containing its microenvironment from the membranes can then be employed further to elucidate not only the array of ligand-binding receptors, but also the nature of the role of the displayed receptor in the life of the cell. Characteristic profiles can thus be obtained for a variety of cells and distinctions made between various differentiated cells, normal cells, diseased cells, tumor cells and the like.

A particularly useful application of the method of the invention is the recovery and identification of peptides associated with HLA class I and class II presentation. In this application, cognate ligands, such as antibodies, directed to antigens encoded by specific MHC haplotypes are coupled to the solid support and incubated with antigen-presenting cells. As a result, a complex is formed between the MHC class I or class II antigen bearing a peptide and the cognate ligand. The complex-containing solid support is then subjected to mechanical disruption to dissociate the complex from the cells, leaving behind the complex of HLA and bound peptide on the support; the peptide can then conveniently be removed from the complex and analyzed. This method can also be applied to, for example, tumor cells to identify peptides presented at the surface which then may be used to elicit a cytotoxic T-cell response to the tumor, since tumor-associated antigens are restricted by MHC.

Other applications include recovery of antigens specific to particular cells, such as Prostate Stem Cell Antigen (PSCA), Prostate Membrane-Specific Antigen (PMSA), various lymphocyte markers such as CD34, CD8, CD4, CD10 and the like, immunoglobulins characteristic of B cells, retinoid receptors, opioid receptors growth factor receptors, ion channels, integrins and the like.

Thus, the method of the invention can be used to identify cellular components associated with signal transduction pathways, such as that associated with EGF activation of the EGF receptor. Antibodies are used to obtain the EGF receptor along with its microenvironment and the components associated with the EGF receptor are analyzed to identify and characterize them.

What is claimed is:

1. A method to isolate and characterize a membrane-bound receptor along with its microenvironment which method comprises providing a solid support coupled to a ligand which specifically binds said receptor, wherein said ligand is a cognate binding agent other than a lectin;

treating said solid support with a sample comprising nucleated cells or organelles thereof comprising said membrane-bound receptors, and which cells or organelles have not been surface-treated, wherein a complex is formed between said membrane-bound receptor and the ligand thus generating a ligand/receptor complex comprising the receptor and its microenvironment, wherein the microenvironment includes additional non-covalently associated cellular components, which complex is coupled to solid support through the ligand thus providing a complexed solid support;

separating the complexed solid support from the remainder of the sample;

subjecting the separated complexed solid support to a force sufficient to dissociate the receptor and its microenvironment from the membrane but insufficient to disrupt the ligand/receptor complex, thus obtaining complexed solid support coupled to a ligand/receptor complex whereby the receptor retains its microenvironment but is separated from the membrane, removing the ligand/receptor complex comprising the receptor and its microenvironment from the complexed solid support; and analyzing the microenvironment of the receptor, wherein the microenvironment is analyzed by chromatographic analysis or mass spectrometry, whereby a membrane-bound receptor along with its microenvironment is isolated and characterized.

2. The method of claim 1 wherein the cells are vertebrate cells.

3. The method of claim 2 wherein the cells are tumor cells or diseased cells.

4. The method of claim 1 wherein the cells are hematopoietic cells, or cells from adipose, areolar, connective, elastic, epithelial, endothelial, neural, mucous or reticular tissues.

5. The method of claim 1 wherein the ligand is an antibody or an immunospecific portion thereof.

6. The method of claim 1 wherein the receptor comprises an HLA antigen.

7. The method of claim 1 wherein the receptor comprises a tumor associated antigen.

8. The method of claim 1 wherein the receptor is a cytokine receptor, a hormone receptor, an opioid receptor, or a steroid receptor.

9. The method of claim 1 wherein the force is achieved through extrusion.

10. The method of claim 1 wherein the force is achieved through vortexing or shaking.

11. The method of claim 1 wherein the force is achieved through sonication.

12. The method of claim 1 wherein the solid support comprises beads.

13. The method of claim 12 wherein said beads are polyacrylamide beads, polystyrene beads, Sephadex beads, or latex beads.

14. The method of claim 1 wherein the solid support is a multi-well plate.

15. The method of claim 1 wherein the ligand is coupled to solid support through a linker containing a portion cleavable by an enzyme and said removing is effected by exposing said linker to said enzyme.

16. A method to isolate and characterize a membrane-bound receptor along with its microenvironment which method comprises providing a solid support coupled to a ligand which specifically binds said receptor, wherein the ligand is coupled to the solid support through a linker containing a photocleavable portion;

treating said solid support with a sample comprising nucleated cells or organelles thereof comprising said membrane-bound receptors, and which cells or organelles have not been surface-treated, wherein a complex is formed between said membrane-bound receptor and the ligand thus generating a ligand/receptor complex comprising the receptor and its microenvironment, wherein the microenvironment includes non-covalently associated cellular components, which complex is coupled to solid support through the ligand thus providing a complexed solid support;

separating the complexed solid support from the remainder of the sample;

subjecting the separated complexed solid support to a force sufficient to dissociate the receptor and its microenvironment from the membrane but insufficient to disrupt the ligand/receptor complex, thus obtaining complexed solid support coupled to a ligand/receptor complex whereby the receptor retains its microenvironment but is separated from the membrane;

removing the ligand/receptor complex comprising the receptor and its microenvironment from the complexed solid support by exposing the linker to light; and analyzing the microenvironment of the receptor.

17. A method to recover a multiplicity of receptors along with their microenvironments which method comprises:

providing a multiplicity of solid support portions each coupled to a different ligand, wherein said ligand is a cognate binding agent other than a lectin;

treating said multiplicity of solid support portions with a sample comprising nucleated cells that comprise at least two cell surface receptors, wherein said cells are not surface treated under conditions wherein ligand/receptor complexes are formed between said ligands and receptors at said cell surfaces which complexes are coupled to said solid support portions through the ligands, thus providing complexed solid support portions;

removing the complexed solid support portions from the sample;

subjecting the complexed solid support portions to forces sufficient to remove the receptors and their microenvironments, wherein the microenvironment includes additional non-covalently associated cellular components, from the surface of said cells but insufficient to disrupt the ligand/receptor complexes;

removing the ligand/receptor complexes comprising the receptors and their microenvironments from the complexed solid support portions; and analyzing the respective microenvironments of at least two receptors, wherein the microenvironment is analyzed by chromatographic analysis or mass spectrometry, whereby a membrane-bound receptor along with its microenvironment is isolated and characterized.

18. The method of claim 17 which further includes identifying the receptors.

19. The method of claim 18 which further includes organizing the identified receptors into a profile characteristic of the membrane sample.

20. The method of claim 17 wherein said ligands are monoclonal antibodies.

21. The method of claim 17 wherein the ligands are coupled to solid support portions through linkers each containing a site cleavable by an enzyme and said removing is effected by exposing said linkers to said enzyme.

22. The method of claim 17 wherein the cells are vertebrate cells.

23. The method of claim 22 wherein the cells are tumor cells or diseased cells.

24. A method to recover a multiplicity of receptors along with their microenvironments which method comprises:

providing a multiplicity of solid support portions each coupled to a different ligand, wherein the ligands are coupled to the solid support portions through linkers each containing a photocleavable site;

treating said multiplicity of solid support portions with a sample comprising nucleated cells that comprise at least two cell surface receptors, wherein said cells are not surface treated under conditions wherein ligand/receptor complexes are formed between said ligands and receptors at said cell surfaces which complexes are coupled to said solid support portions through the ligands, thus providing complexed solid support portions;

removing the complexed solid support portions from the sample; and subjecting the complexed solid support portions to forces sufficient to remove the receptors and their microenvironments, wherein the microenvironment includes additional non-covalently associated cellular components, from the surface of said cells but insufficient to disrupt the ligand/receptor complexes;

removing the ligand/receptor complexes comprising the receptors and their microenvironments from the complexed solid support portions by exposing the linkers to light; and analyzing the respective microenvironments of at least two receptors.

* * * * *